(12) United States Patent
Kobayashi

(10) Patent No.: US 8,860,018 B2
(45) Date of Patent: Oct. 14, 2014

(54) ANTHANTHRENE BASED COMPOUND AND SEMICONDUCTOR DEVICE

(71) Applicant: Sony Corporation, Tokyo (JP)

(72) Inventor: Norihito Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 20 days.

(21) Appl. No.: 13/713,929

(22) Filed: Dec. 13, 2012

(65) Prior Publication Data

US 2013/0099223 A1    Apr. 25, 2013

Related U.S. Application Data

(62) Division of application No. 12/821,598, filed on Jun. 23, 2010.

(30) Foreign Application Priority Data

Jul. 1, 2009  (JP) .................................. 2009-156459

(51) Int. Cl.
| | | |
|---|---|---|
| H01L 29/80 | (2006.01) | |
| C07D 311/78 | (2006.01) | |
| H01L 51/00 | (2006.01) | |
| C07D 493/06 | (2006.01) | |
| C09K 11/06 | (2006.01) | |
| H05B 33/10 | (2006.01) | |
| H01L 51/05 | (2006.01) | |

(52) U.S. Cl.
CPC ...... *H01L 51/006* (2013.01); *C09K 2211/1088* (2013.01); *C09K 2211/1011* (2013.01); *C07D 493/06* (2013.01); *H01L 51/0558* (2013.01); *H01L 51/0073* (2013.01); *C09K 11/06* (2013.01); *H05B 33/10* (2013.01)
USPC ............................................ 257/40; 549/381

(58) Field of Classification Search
USPC ............................................ 257/40; 549/381
See application file for complete search history.

(56) References Cited

U.S. PATENT DOCUMENTS 8,114,531 B2 *   2/2012   Stoessel et al. ............... 428/690

FOREIGN PATENT DOCUMENTS

| DE | 102006035035 | 1/2008 |
|---|---|---|
| JP | 2004-107257 | 4/2004 |
| WO | WO 2008/011964 A1 * | 1/2008 |

OTHER PUBLICATIONS

Suresh, et al., Journal of Organic Chemistry, "Clar's Aromatic Sextet Theory Revisited Via Molecular Electrostatic Potential Typography", 1999, vol. 64, pp. 2505-2512.
Journal of the American Chemical Society, "Circuit Resonance Energy", 2006, vol. 128, pp. 2873-2879.
Angewante Chemie, "Approach for Organic Field-Effect Transistors." International Edition, 2003, vol. 42, pp. 1159-1162.
Journal of Applied Physics, "Organic Thin-Film transistors based on Anthracene Oligomers", 2004, vol. 95, pp. 5795-5799.
European Search Report dated Nov. 23, 2010 based on European Patent Appln. No. 10006018.5.

* cited by examiner

*Primary Examiner* — T. Victor Oh
(74) *Attorney, Agent, or Firm* — K&L Gates LLP

(57) ABSTRACT

An anthanthrene based compound of the structural formula (1) is disclosed:

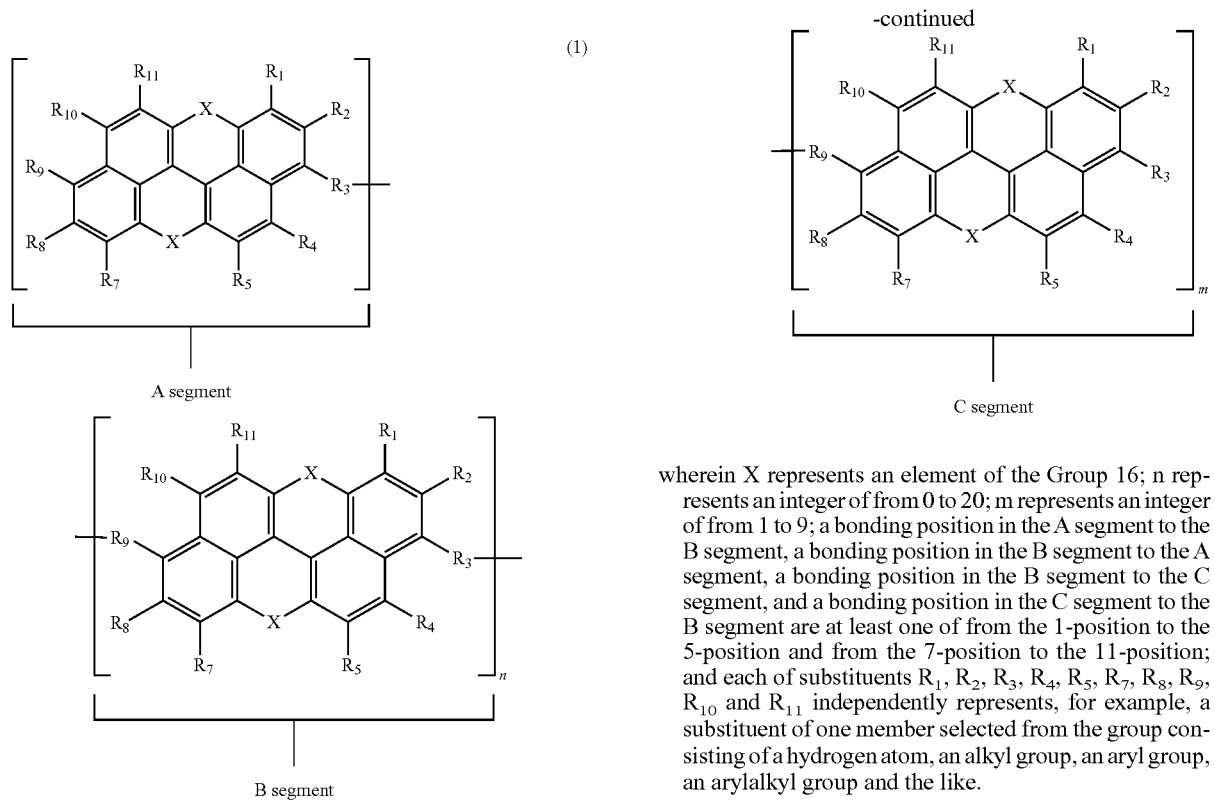

wherein X represents an element of the Group 16; n represents an integer of from 0 to 20; m represents an integer of from 1 to 9; a bonding position in the A segment to the B segment, a bonding position in the B segment to the A segment, a bonding position in the B segment to the C segment, and a bonding position in the C segment to the B segment are at least one of from the 1-position to the 5-position and from the 7-position to the 11-position; and each of substituents $R_1$, $R_2$, $R_3$, $R_4$, $R_5$, $R_7$, $R_8$, $R_9$, $R_{10}$ and $R_{11}$ independently represents, for example, a substituent of one member selected from the group consisting of a hydrogen atom, an alkyl group, an aryl group, an arylalkyl group and the like.

1 Claim, 3 Drawing Sheets

ANTHANTHRENE BASED COMPOUND AND SEMICONDUCTOR DEVICE

CROSS REFERENCES TO RELATED APPLICATIONS

The present application is a divisional of U.S. application Ser. No. 12/821,598, filed on Jun. 23, 2010, which claims priority to Japanese Priority Patent Application JP 2009-156459 filed in the Japan Patent Office on Jul. 1, 2009, the entire contents of which is hereby incorporated by reference.

BACKGROUND

The present application relates to an anthanthrene based compound and a semiconductor device including a semiconductor layer composed of such an anthanthrene based compound.

In recent years, semiconductor devices including a semiconductor layer composed of an organic semiconductor material have been receiving considerable attention. In such a semiconductor device, a semiconductor layer can be coated and deposited at a low temperature as compared with a configuration including a semiconductor layer composed of an inorganic material. For that reason, such a semiconductor device is advantageous for realizing a large area and can be formed on a flexible substrate which is, however, low in heat resistance, such as plastics. Reduction in cost as well as multi-functionalization is also expected.

At present, as organic semiconductor materials constituting a semiconductor layer, for example, polyacene compounds such as anthracene, naphthacene and pentacene having the following structural formulae are being widely researched.

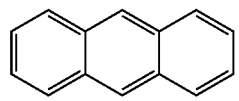

Anthracene

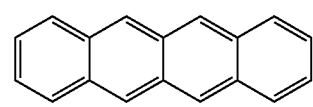

Tetracene
(naphthacene)

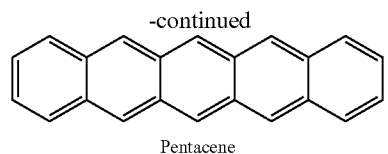

Pentacene

In these polyacene compounds, it is expected that as the ring length elongates, a π-system becomes wide, and larger overlapping of orbits is formed between adjacent molecules, whereby carrier mobility is enhanced. However, in general, it may be said that pentacene is an acene compound having a maximum ring length at which it is able to stably exist and that polyacene compounds having a loner ring length than hexacene are instable. For that reason, it is difficult to isolate such a polyacene compound (see Journal of Organic Chemistry, 1999, Vol. 64, pp. 2505 to 2512; and Journal of The American Chemical Society, 2006, Vol. 128, pp. 2873 to 2879). Also, as means for constructing a wide π-system, there are reported oligo polyacene compounds resulting from bonding plural polyacene compounds (see JP-A-2004-107257; *Angewante Chemie, International Edition*, 2003, Vol. 42, pp. 1159 to 1162; and *Journal of Applied Physics*, 2004, Vol. 95, pp. 5795 to 5799).

SUMMARY

However, the polyacene compound as a constituent unit has reaction active sites within a molecule thereof (specifically, for example, so far as pentacene is concerned, an electron density is high at the 6-position and the 12-position, and the 6-position and the 12-position are a reaction active site) and easily causes a decomposition reaction by oxygen, light, water, high temperature or the like, and its stability in the atmosphere is not satisfactory. Then, even in an oligo polyacene compound, so far as it has such a polyacene compound, it may be considered that it is difficult to establish stability of the molecule.

Accordingly, it is desirable to provide an anthanthrene based compound having favorable stability in the atmosphere and a semiconductor device including a semiconductor layer composed of such an anthanthrene based compound.

According to a first embodiment, there is provided an anthanthrene based compound represented by the following structural formula (1) (oligo dichalcogeno anthanthrene based compound).

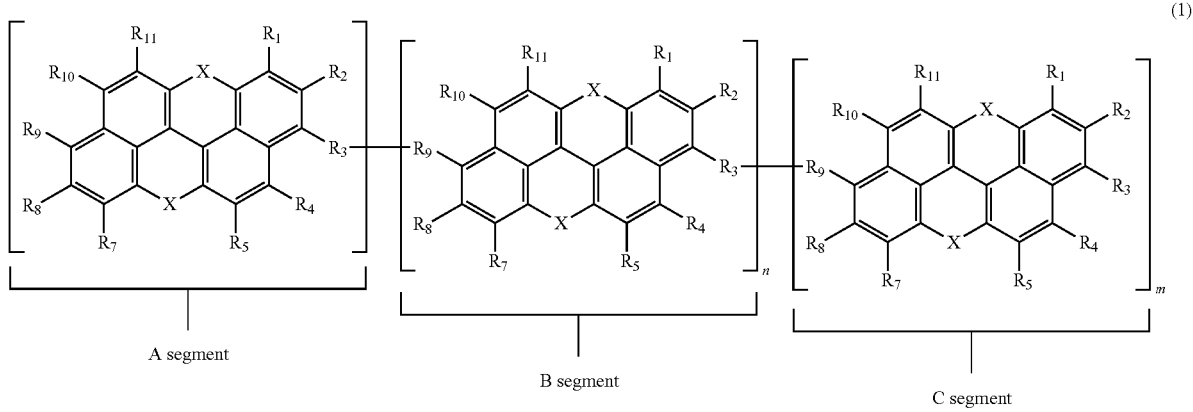

(1)

According to a second embodiment, there is provided an anthanthrene based compound represented by the following structural formula (2) (oligo dichalcogeno anthanthrene based compound).

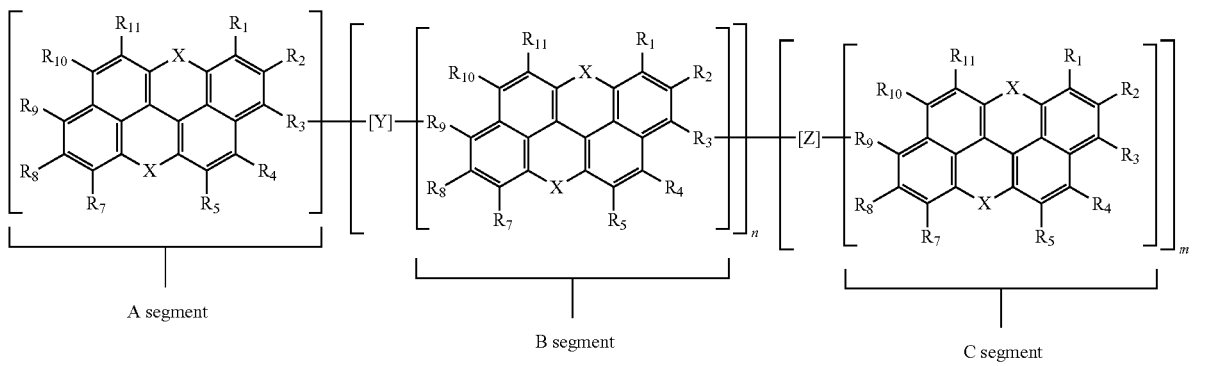

A segment

B segment

C segment (2)

According to the first embodiment, there is also provided a semiconductor device including a substrate having thereon a gate electrode, a gate insulating layer, source/drain electrodes and a channel-forming region, wherein the channel-forming region is composed of the anthanthrene based compound (oligo dichalcogeno anthanthrene based compound) according to the foregoing first embodiment.

According to the second embodiment, there is also provided a semiconductor device including a substrate having thereon a gate electrode, a gate insulating layer, source/drain electrodes and a channel-forming region, wherein the channel-forming region is composed of the anthanthrene based compound (oligo dichalcogeno anthanthrene based compound) according to the foregoing second embodiment.

In the anthanthrene based compound according to the first embodiment, or the anthanthrene based compound constituting the channel-forming region of the semiconductor device according to the first embodiment, X represents an element belonging to the Group 16;

n represents an integer of from 0 to 20;

m represents an integer of from 1 to 9;

a bonding position in the A segment to the B segment is at least one of from the 1-position to the 5-position and from the 7-position to the 11-position;

a bonding position in the B segment to the A segment is at least one of from the 1-position to the 5-position and from the 7-position to the 11-position;

a bonding position in the B segment to the C segment is at least one of from the 1-position to the 5-position and from the 7-position to the 11-position; and a bonding position in the C segment to the B segment is at least one of from the 1-position to the 5-position and from the 7-position to the 11-position.

The bonding position in the A segment to the B segment is not always required to be identical with the bonding position in the B segment to the C segment; and the bonding position in the B segment to the C segment is not always required to be identical with the bonding position in the C segment to the B segment. Here, in the case of n=0, as a matter of course, a different reading is given such that the bonding position in the A segment to the C segment is at least one of from the 1-position to the 5-position and from the 7-position to the 11-position; and that the bonding position in the C segment to the A segment is at least one of from the 1-position to the 5-position and from the 7-position to the 11-position. Also, in the case where n is 2 or more, the B segments may be linearly bonded to each other as a kind, may be bonded to each other in a partially branched state, or may be cyclically bonded to each other as a kind In the case where m is 2 or more, similarly, the C segments may be linearly bonded to each as a kind, may be bonded to each other in a partially branched state, or may be cyclically bonded to each other as a kind Also, in the anthanthrene based compound according to the second embodiment, or the anthanthrene based compound constituting the channel-forming region of the semiconductor device according to the second embodiment, X represents an element belonging to the Group 16;

each of [Y] and [Z] independently represents a functional group of one member selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, an sulfinyl group, an alkylsulfonyl group, an arylsulfonyl group, an amino group, a fluorinated hydrocarbon group, a cyano group, a nitro group, a hydroxyl group, a mercapto group and a silyl group;

n represents an integer of from 0 to 20;

m represents an integer of from 1 to 9;

a bonding position in the A segment to [Y] is at least one of from the 1-position to the 5-position and from the 7-position to the 11-position;

a bonding position in the B segment to [Y] is at least one of from the 1-position to the 5-position and from the 7-position to the 11-position;

a bonding position in the B segment to [Z] is at least one of from the 1-position to the 5-position and from the 7-position to the 11-position; and a bonding position in the C segment to [Z] is at least one of from the 1-position to the 5-position and from the 7-position to the 11-position.

The bonding position in the A segment to [Y] is not always required to be identical with the bonding position in the B segment to [Y]; and the bonding position in the B segment to [Z] is not always required to be identical with the bonding position in the C segment to [Z]. Here, in the case of n=0, as a matter of course, a different reading is given such that the bonding position in the A segment to [Z] is at least one of from the 1-position to the 5-position and from the 7-position to the 11-position; and that the bonding position in the C segment to [Z] is at least one of from the 1-position to the 5-position and from the 7-position to the 11-position. Also, a bonding position in [Y] to the A segment, a bonding position in [Y] to the B segment, a bonding position in [Z] to the B segment and a bonding position in [Z] to the C segment are not important. In the case where n is 2 or more, the B segments may be linearly bonded to each other as a kind, may be bonded to each other in a partially branched state, or may be cyclically bonded to each other as a kind. In the case where m is 2 or more, similarly, the C segments may be linearly bonded to each as a kind, may be bonded to each other in a partially branched state, or may be cyclically bonded to each other as a kind.

Furthermore, in the anthanthrene based compound according to the first embodiment or second embodiment, each of substituents $R_1$, $R_2$, $R_3$, $R_4$, $R_5$, $R_7$, $R_8$, $R_9$, $R_{10}$ and $R_{11}$ independently represents a substituent of one member selected from the group consisting of a hydrogen atom, an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, a sulfinyl group, an alkylsulfonyl group, an arylsulfonyl group, an amino group, a halogen atom, a fluorinated hydrocarbon group, a cyano group, a nitro group, a hydroxyl group, a mercapto group and a silyl group. In the anthanthrene based compound, etc. according to the embodiment, it is more preferable that each of the substituents $R_1$, $R_2$, $R_3$, $R_4$, $R_5$, $R_7$, $R_8$, $R_9$, $R_{10}$ and $R_{11}$ independently represents a substituent selected from the group consisting of an alkyl group, an alkenyl group, an aryl group, an arylalkyl group, an aromatic heterocyclic ring and a halogen atom.

Here, examples of the alkyl group include a methyl group, an ethyl group, a propyl group, an isopropyl group, a tert-butyl group, a pentyl group, a hexyl group, an octyl group and a dodecyl group. It is not important whether the alkyl group is linear or branched. Also, examples of the cycloalkyl group include a cyclopentyl group and a cyclohexyl group; examples of the alkenyl group include a vinyl group; examples of the alkynyl group include an ethynyl group; examples of the aryl group include a phenyl group and a naphthyl group; examples of the arylalkyl group include a methylaryl group, an ethylaryl group, an isopropylaryl group and an n-butylaryl group; examples of the aromatic heterocyclic ring include a pyridyl group, a thienyl group, a furyl group, a pyridazinyl group, a pyrimidinyl group, a pyrazinyl group, a triazinyl group, an imidazolyl group, a pyrazolyl group, a thiazolyl group, a quinazolinyl group and a phthalazinyl group; examples of the heterocyclic group include a pyrrolidyl group, an imidazolidyl group, a morpholyl group and an oxazolidyl group; examples of the alkoxy group include a methoxy group, an ethoxy group, a propyloxy group, a pentyloxy group and a hexyloxy group; examples of the cycloalkoxy group include a cyclopentyloxy group and a cyclohexyloxy group; examples of the aryloxy group include a phenoxy group and a naphthyloxy group; examples of the alkylthio group include a methylthio group, an ethylthio group, a propylthio group, a pentylthio group and a hexylthio group; examples of the cycloalkylthio group include a cyclopentylthio group and a cyclohexylthio group; examples of the arylthio group include a phenylthio group and a naphthylthio group; examples of the alkoxycarbonyl group include a methyloxycarbonyl group, an ethyloxycarbonyl group, a butyloxycarbonyl group and an octyloxycarbonyl group; examples of the aryloxycarbonyl group include a phenyloxycarbonyl group and a naphthyloxycarbonyl group; examples of the sulfamoyl group include an aminosulfonyl group, a methylaminosulfonyl group, a dimethylaminosulfonyl group, a cyclohexylaminosulfonyl group, a phenylaminosulfonyl group, a naphthylaminosulfonyl group and a 2-pyridylaminosulfonyl group; examples of the acyl group include an acetyl group, an ethylcarbonyl group, a propylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group and a pyridylcarbonyl group; examples of the acyloxy group include an acetyloxy group, an ethylcarbonyloxy group, an octylcarbonyloxy group and a phenylcarbonyloxy group; examples of the amide group include a methylcarbonylamino group, an ethylcarbonylamino group, a dimethylcarbonylamino group, a pentylcarbonylamino group, a cyclohexylcarbonylamino group, a 2-ethylhexylcarbonylamino group, a phenylcarbonylamino group and a naphthylcarbonylamino group; examples of the carbamoyl group include an aminocarbonyl group, a methylaminocarbonyl group, a dimethylaminocarbonyl group, a cyclohexylaminocarbonyl group, a 2-ethylhexylaminocarbonyl group, a phenylaminocarbonyl group, a naphthylaminocarbonyl group and a 2-pyridylaminocarbonyl group; examples of the ureido group include a methylureido group, an ethylureido group, a cyclohexylureido group, a dodecylureido group, a phenylureido group, a naphthylureido group and a 2-pyridylaminoureido group; examples of the sulfinyl group include a methylsulfinyl group, an ethylsulfinyl group, a butylsulfinyl group, a cyclohexylsulfinyl group, a 2-ethylhexylsulfinyl group, a phenylsulfinyl group, a naphthylsulfinyl group and a 2-pyridylsulfinyl group; examples of the alkylsulfonyl group include a methylsulfonyl group, an ethylsulfonyl group, a butylsulfonyl group, a cylohexylsulfonyl group, a 2-ethylhexylsulfonyl group and a dodecylsulfonyl group; examples of the arylsulfonyl group include a phenylsulfonyl group, a naphthylsulfonyl group and a 2-pyridylsulfonyl group; examples of the amino group include an amino group, an ethylamino group, a dimethylamino group, a butylamino group, a 2-ethylhexylamino group, an anilino group, a naphthylamino group and a 2-pyridylamino group; examples of the halogen atom include a fluorine atom, a chlorine atom, a bromine atom and an iodine atom; and examples of the fluorinated hydrocarbon group include a fluoromethyl group, a trifluoromethyl group, a pentafluoroethyl group and a pentafluorophenyl group. Furthermore, there can be exemplified a cyano group, a nitro group, a hydroxyl group and a mercapto group. Examples of the silyl group include a trimethylsilyl group, a triisopropylsilyl group, a triphenylsilyl group and a phenyldiethylsilyl group. Here, each of the above-exemplified substituents may be further substituted with any of the foregoing substituents. Also, a plurality of these substituents may be bonded to each other to form a ring.

In the anthanthrene based compound according to an embodiment including the foregoing preferred modes, a mode wherein X is an oxygen atom is much more preferable.

In the anthanthrene based compound according to an embodiment, a repeating unit (monomer unit) is stable in the atmosphere, and the repeating unit (monomer unit) has a wide π-system (having more aromatic rings). That is, each of the carbon atoms at the 6-position and the 12-position of the monomer unit in the anthanthrene based compound, etc. according to the embodiment is substituted with an element belonging to the Group 16, and therefore, the 6-position and the 12-position are not a reaction active site. Thus, the compound hardly causes a decomposition reaction by oxygen, light, water, high temperature or the like and is excellent in stability in the atmosphere. Also, larger overlapping of orbits is formed between adjacent molecules, and carrier mobility can be enhanced. That is, according to the embodiments, it is possible to provide a stable organic semiconductor material having high oxygen resistance, light fastness, heat resistance, water resistance and solvent resistance in the atmosphere and also having high carrier mobility. Therefore, by constituting a channel-forming region from the anthanthrene based compound, etc. according to the embodiment, the semiconductor device (organic transistor) according to the embodiment is able to display high carrier mobility and even after a thermal treatment at a high temperature in the atmosphere, is able to maintain high stability and high carrier mobility. Also, the anthanthrene based compound, etc. according to the embodiment has high stability, and therefore, it is possible to widen a width of a manufacturing process of a semiconductor device Additional features and advantages are described herein, and will be apparent from the following Detailed Description and the figures.

DETAILED DESCRIPTION

Figure 1A:
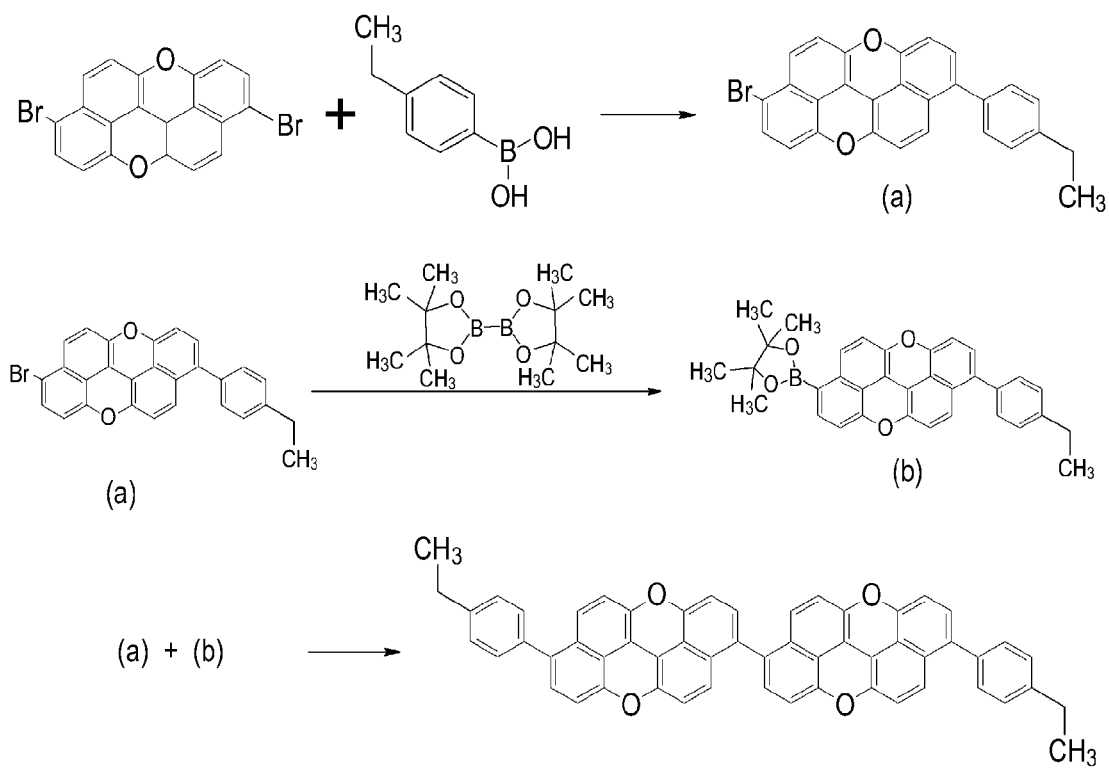
FIG. 1A and FIG. 1B are drawings showing synthesis schemes of anthanthrene based compounds of Example 1 and Example 2, respectively.

The present application is described below in detail with reference to the drawings according to an embodiment. The detailed description is provided as follows:
1. Anthanthrene based compound according to the first embodiment; anthanthrene based compound according to the second embodiment; semiconductor device according to the first embodiment; semiconductor device according to the second embodiment; and explanation regarding the whole thereof.
2. Example 1 (Anthanthrene based compound according to the first embodiment)
3. Example 2 (Modification of Example 1)
4. Example 3 (Anthanthrene based compound according to the second embodiment)
5. Example 4 (Semiconductor devices according to the first embodiment and second embodiment and others)

In the anthanthrene based compound according to the embodiment, X represents an element belonging to the Group 16. The "element belonging to the Group 16" as referred to herein is a generic name of elements belonging to the Group 16 of the periodic table; and oxygen (O), sulfur (S), selenium (Se), tellurium (Te) and polonium (Po) are classified in this. This element is also called an oxygen group element or a chalcogen. Also, each of the A segment, the B segment and the C segment per se is an organic semiconductor material obtained by substituting a dioxaanthanthrene based compound, specifically 6,12-dioxaanthanthrene (so-called perixanthenoxanthene, which is sometimes abbreviated as "PXX") at from the 1-position to the 5-position and from the 7-position to the 11-position with any of the following substituents including a hydrogen atom.

In the case where the semiconductor device according to the first embodiment or second embodiment (which will be hereinafter sometimes generically referred to simply as "semiconductor device according to the embodiment") is constituted of a bottom gate/bottom contact type field effect transistor (FET), such a bottom gate/bottom contact type FET includes (A) a gate electrode formed on a substrate;
(B) a gate insulating layer formed on the gate electrode;
(C) source/drain electrodes formed on the gate insulating layer; and
(D) a channel-forming region located between the source/drain electrodes and formed on the gate insulating layer.

Alternatively, in the case where the semiconductor device according to the embodiment is constituted of a bottom gate/top contact type FET, such a bottom gate/top contact type FET includes (A) a gate electrode formed on a substrate;
(B) a gate insulating layer formed on the gate electrode;
(C) a channel-forming region and a channel-forming region extension formed on the gate insulating layer; and
(D) source/drain electrodes formed on the channel-forming region extension.

Alternatively, in the case where the semiconductor device according to the embodiment is constituted of a top gate/bottom contact type FET, such a top gate/bottom contact type FET includes (A) source/drain electrodes formed on a substrate;
(B) a channel-forming region formed on the substrate located between the source/drain electrodes;
(C) a gate insulating layer formed on the channel-forming region; and
(D) a gate electrode formed on the gate insulating layer.

Alternatively, in the case where the semiconductor device according to the embodiment is constituted of a top gate/top contact type FET, such a top gate/top contact type FET includes (A) a channel-forming region and a channel-forming region extension formed on a substrate;
(B) source/drain electrodes formed on the channel-forming region extension;
(C) a gate insulating layer formed on the source/drain electrodes and the channel-forming region; and
(D) a gate electrode formed on the gate insulating layer.

Here, the substrate can be constituted of a silicon oxide based material (for example, $SiO_X$ and spin-on glass (SOG)); silicon nitride ($SiN_Y$); aluminum oxide ($Al_2O_3$); or a metal oxide high-dielectric constant insulating film. In the case where the substrate is constituted of such a material, the substrate may be formed on a support (or in an upper part of a support) which is properly selected among the following materials. That is, examples of the support and/or a substrate other than the foregoing substrate include organic polymers such as polymethyl methacrylate (polymethacrylic acid methyl (PMMA)), polyvinyl alcohol (PVA), polyvinyl phenol (PVP), polyethersulfone (PES), polyimide, polycarbonate, polyethylene terephthalate (PET) and polyethylene naphthalate (PEN) (having a mode of a polymer material such as flexible plastic films, plastic sheets or plastic substrates constituted of a polymer material); and mica. By using a substrate constituted of such a flexible polymer material, for example, the semiconductor device can be built in or integrated into a display device or an electronic appliance having a curved shape. Other examples of the substrate include various glass substrates, various glass substrates provided with an insulating film on the surface thereof, quartz substrates, quartz substrates provided with an insulating film on the surface thereof, silicon substrates provided with an insulating film on the surface thereof and metal substrates made of an alloy of every kind or a metal of every kind, such as stainless steel. As a support having electrical insulating properties, an appropriate material may be selected among the foregoing materials. Other examples of the support include conductive substrates (for example, a substrate made of a metal (e.g., gold), a substrate made of highly oriented graphite, a stainless steel substrate, etc.). Also, depending upon the configuration and structure of the semiconductor device, the semiconductor device may be provided on a support. Such a support can be made of any of the foregoing materials.

Examples of the material constituting the gate electrode, source/drain electrodes and wirings include metals such as platinum (Pt), gold (Au), palladium (Pd), chromium (Cr), molybdenum (Mo), nickel (Ni), aluminum (Al), silver (Ag), tantalum (Ta), tungsten (W), copper (Cu), titanium (Ti), indium (In) and tin (Sn); an alloy containing such a metal element; conductive particles composed of such a metal; conductive particles composed of alloys containing such a metal; and conductive materials such as impurity-containing polysilicon. A laminated structure including layers each containing such an element may be employed. Furthermore, as the material constituting the gate electrode, source/drain electrodes and wirings, an organic material (conductive polymer) such as poly(3,4-ethylenedioxythiophene)/polystyrene sulfonic acid [PEDOT/PSS] can also be exemplified. The materials constituting the gate electrode, source/drain electrodes and wirings may be the same or different.

Though a method for forming the gate electrode, source/drain electrodes and wiring varies depending upon the materials constituting them, examples thereof include a physical vapor deposition method (PVD method); various chemical vapor deposition methods (CVD methods) inclusive of an MOCVD method; a spin coating method; various printing methods such as a screen printing method, an inkjet printing method, an offset printing method, a reverse offset printing method, a gravure printing method and a microcontact method; various coating methods such as an air doctor coating method, a blade coating method, a rod coating method, a knife coating method, a squeeze coating method, a reverse roll coating method, a transfer roll coating method, a gravure coating method, a kiss coating method, a cast coating method, a spray coating method, a slit orifice coating method, a calender coating method and a dipping method; a stamping method; a lift-off method; a shadow mask method; plating methods such as an electrolytic plating method, an electroless plating method and a combination thereof; and a spraying method. If desired, such a method may be combined with a patterning technique. Furthermore, examples of the PVD methods include (a) various vacuum vapor deposition methods such as an electron beam heating method, a resistance heating method, a flash vapor deposition method and a method of heating a crucible; (b) a plasma vapor deposition method; (c) various sputtering methods such as a diode sputtering method, a direct current sputtering method, a direct current magnetron sputtering method, a radio frequency sputtering method, a magnetron sputtering method, an ion beam sputtering method and a bias sputtering method; and (d) various ion plating methods such as a direct current (DC) method, an RF method, a multi-cathode method, an activation reaction method, an electric field vapor deposition method, a radio frequency ion plating method and a reactive ion plating method.

Furthermore, examples of the material constituting the gate insulating layer include inorganic insulating materials such as silicon oxide based materials, silicon nitride ($SiN_Y$) and metal oxide high-dielectric constant insulating films; and organic insulating materials such as polymethyl methacrylate (PMMA), polyvinyl phenol (PVP) and polyvinyl alcohol (PVA). These materials may be used in combinations. Examples of the silicon oxide based material include silicon oxide ($SiO_X$), BPSG, PSG, BSG, AsSG, PbSG, silicon oxynitride (SiON), SOG (spin-on glass) and low-dielectric constant materials (for example, polyaryl ethers, cycloperfluorocarbon polymers, benzocyclobutene, cyclic fluorocarbon resins, polytetrafluoroethylene, fluoroaryl ethers, polyfluoroimide, amorphous carbon and organic SOG).

Alternatively, the gate insulating layer can be formed by oxidizing or nitriding the surface of the gate electrode, or can be obtained by depositing an oxide film or a nitride film on the surface of the gate electrode. A method for oxidizing the surface of the gate electrode varies depending upon the material constituting the gate electrode, and examples thereof include an oxidation method using $O_2$ plasma and an anodic oxidation method. Also, a method for nitriding the surface of the gate electrode varies depending upon the material constituting the gate electrode, and examples thereof include a nitriding method using $N_2$ plasma. Alternatively, for example, when a gate electrode made of Au is used, a gate insulating layer can be formed in a self-assembling manner on the surface of the gate electrode by coating the surface of the gate electrode with an insulating molecule having a functional group capable of forming a chemical bond with the gate electrode, such as linear hydrocarbons whose one end is modified with a mercapto group, by a method such a dipping method.

Examples of a method for forming the channel-forming region, or the channel-forming region and the channel-forming region extension, include the foregoing various PVD methods; a spin coating method; the foregoing various printing methods; the foregoing various coating methods; a dipping method; a casting method; and a spraying method. According to circumstances, additives (for example, so-called doping materials such as n-type impurities and p-type impurities) can be added to the anthanthrene based compound according to the first embodiment or second embodiment.

In the case where the semiconductor device according to the embodiment is applied to and used for display devices or various electronic appliances, a monolithic integrated circuit in which a number of semiconductor devices are integrated on a support may be fabricated, or the individual semiconductor devices may be used upon being separated by cutting to produce discrete components. Also, the semiconductor device may be sealed with a resin. Specifically, the semiconductor device according to the embodiment can be used for liquid crystal display devices, organic electroluminescent light-emitting apparatuses, electronic papers, various sensors, RFIDs (radio frequency identification card) and the like.

EXAMPLE 1

Example 1 is concerned with the anthanthrene based compound according to the first embodiment. The anthanthrene based compound of Example 1 is an anthanthrene based compound represented by the following structural formula (1) (oligo dichalcogeno anthanthrene based compound).

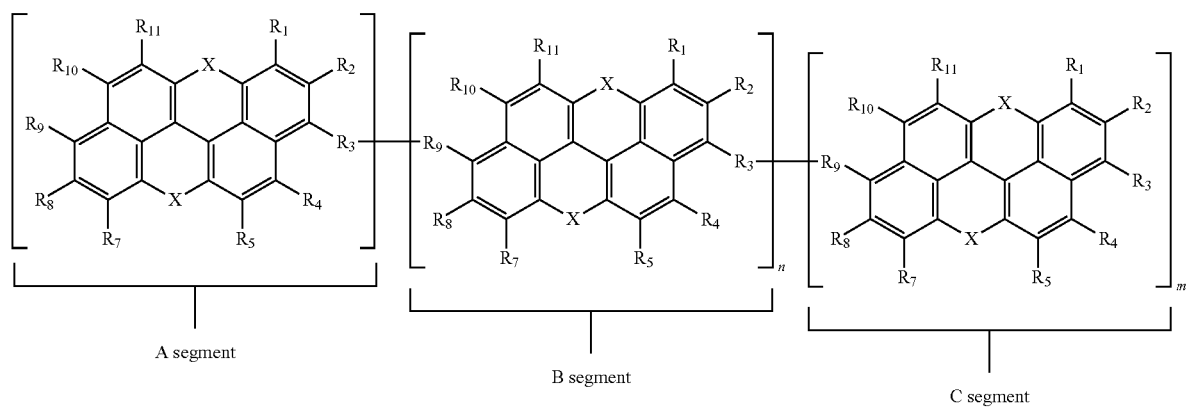

(1)

Each of the A segment, the B segment and the C segment per se is an organic semiconductor material obtained by substituting a dioxaanthanthrene based compound, specifically 6,12-dioxaanthanthrene (so-called peri-xanthenoxanthene, "PXX") at from the 1-position to the 5-position and from the 7-position to the 11-position with any of the foregoing substituents including a hydrogen atom. Here, X represents an element belonging to the Group 16; n represents an integer of from 0 to 20; and m represents an integer of from 1 to 9.

Also, a bonding position in the A segment to the B segment is at least one of from the 1-position to the 5-position and from the 7-position to the 11-position; a bonding position in the B segment to the A segment is at least one of from the 1-position to the 5-position and from the 7-position to the 11-position; a bonding position in the B segment to the C segment is at least one of from the 1-position to the 5-position and from the 7-position to the 11-position; and a bonding position in the C segment to the B segment is at least one of from the 1-position to the 5-position and from the 7-position to the 11-position.

In Example 1, X is an oxygen (O) element; n is 0; and m is 1. Therefore, the B segment does not exist; and a different reading is given such that a bonding position in the A segment to the C segment is at least one of from the 1-position to the 5-position and from the 7-position to the 11-position; and that a bonding position in the C segment to the A segment is at least one of from the 1-position to the 5-position and from the 7-position to the 11-position. Specifically, the bonding position in the A segment to the C segment is one site at the 3-position; and the bonding position in the C segment to the A segment is one site at the 10-position. Also, in the A segment, each of the substituents $R_1$, $R_2$, $R_4$, $R_5$, $R_7$, $R_8$, $R_{10}$ and $R_{11}$ is a hydrogen atom; and $R_9$ is an arylalkyl group, specifically, an ethylaryl group, and more specifically an ethylphenyl group. Also, in the C segment, each of the substituents $R_1$, $R_2$, $R_4$, $R_5$, $R_7$, $R_8$, $R_{10}$ and $R_{11}$ is a hydrogen atom; and $R_3$ is an arylalkyl group, specifically, an ethylaryl group, and more specifically an ethylphenyl group.

More specifically, the anthanthrene based compound of Example 1 is represented by the following structural formula (3). Also, a synthesis scheme of the anthanthrene based compound of Example 1 is shown in FIG. 1A. That is, equivalent amounts of 3,9-dibromo-peri-xanthenoxanthene and p-ethylphenyl boronic acid are subjected to the Suzuki-Miyaura cross-coupling reaction (see Miyaura, N. and Suzuki, A., *J. Chem. Soc., Chem. Commun.,* 1979, 866; and Miyaura, N., Yamada, K. and Suzuki, A., *Tetrahedron Lett.,* 1979, 3437) in the presence of a palladium catalyst, thereby obtaining a compound (a). Subsequently, the compound (a) and 0.5 equivalents of bis(pinacolato)diboron are subjected to the Suzuki-Miyaura cross-coupling reaction in the presence of a palladium catalyst, thereby obtaining a compound (b). Furthermore, equivalent amounts of the compound (a) and the compound (b) are subjected to the Suzuki-Miyaura cross-coupling reaction in the presence of a palladium catalyst, whereby a compound represented by the structural formula (3) can be obtained.

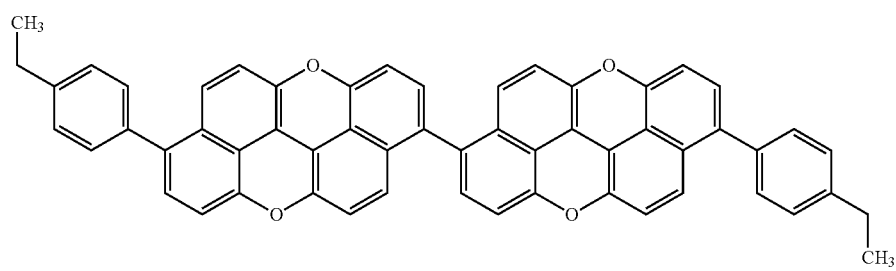

(3)

In the anthanthrene based compound of Example 1 or each of Examples 2 to 3 as described later, a repeating unit (monomer unit) is stable in the atmosphere. That is, since the carbon atoms at the 6-position and the 12-position of the monomer unit (a major skeleton thereof is constituted of PXX) in Example 1 or each of Examples 2 to 3 as described later are substituted with an element belonging to the Group 16 (specifically, an oxygen element), the instant sites are no longer a reaction active site; and the compound hardly causes a decomposition reaction by oxygen, light, water, high temperature or the like and is excellent in stability in the atmosphere. Also, the repeating unit (monomer unit) has a wide π-system. That is, the compound has more aromatic rings, and its π-electron conjugated region is widened. Accordingly, the anthanthrene based compound of Example 1 or each of Examples 2 to 3 as described later forms larger overlapping of orbits between adjacent molecules (a so-called π-π stack, etc.), and its carrier mobility can be enhanced. That is, according to Example 1 or Examples 2 to 3 as described later, it is possible to provide a stable organic semiconductor material having high oxygen resistance, light fastness, heat resistance, water resistance and solvent resistance in the atmosphere and also having high carrier mobility. Therefore, as described later, by constituting a channel-forming region of an organic transistor from the anthanthrene based compound of Example 1 or each of Examples 2 to 3 as described later, the organic transistor is able to display high carrier mobility and even after a thermal treatment at a high temperature in the atmosphere, is able to maintain high stability and high carrier mobility. Also, the anthanthrene based compound of Example 1 or each of the Examples 2 to 3 as described later has high stability, and therefore, it is possible to widen a width of a manufacturing process of a semiconductor device.

EXAMPLE 2

Example 2 is a modification of Example 1. In Example 1, n was set to be 0, whereas in Example 2, n was set to be 1.

Specifically, a bonding position in the A segment to the B segment is one site at the 3-position; and a bonding position in the B segment to the A segment is one site at the 10-position. Also, a bonding position in the B segment to the C segment is one site at the 3-position; and a bonding position in the C segment to the B segment is one site at the 10-position. In the A segment, each of the substituents $R_1, R_2, R_4, R_5, R_7, R_8, R_{10}$ and $R_{11}$ is a hydrogen atom; and $R_9$ is an arylalkyl group, specifically, an ethylaryl group, and more specifically an ethylphenyl group. Also, in the B segment, each of the substituents $R_1, R_2, R_4, R_5, R_7, R_8, R_{10}$ and $R_{11}$ is a hydrogen atom. Furthermore, in the C segment, each of the substituents $R_1, R_2, R_4, R_5, R_7, R_8, R_{10}$ and $R_{11}$ is a hydrogen atom; and $R_3$ is an arylalkyl group, specifically, an ethylaryl group, and more specifically an ethylphenyl group.

Figure 1B:
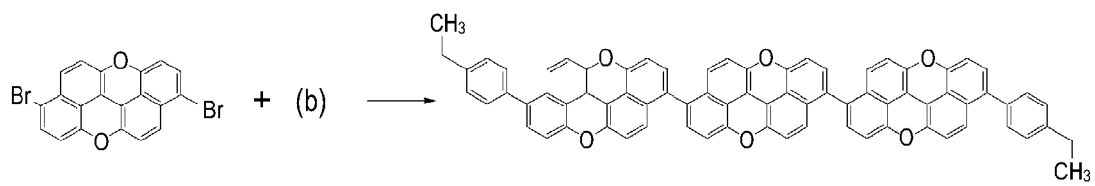

More specifically, the anthanthrene based compound of Example 2 is represented by the following structural formula (4). Also, a synthesis scheme of the anthanthrene based compound of Example 2 is shown in FIG. 1B. That is, 3,9-dibromo-peri-xanthenoxanthene and 2 equivalents of the compound (b) are subjected to the Suzuki-Miyaura cross-coupling reaction in the presence of a palladium catalyst, whereby a compound represented by the structural formula (4) can be obtained.

(4)

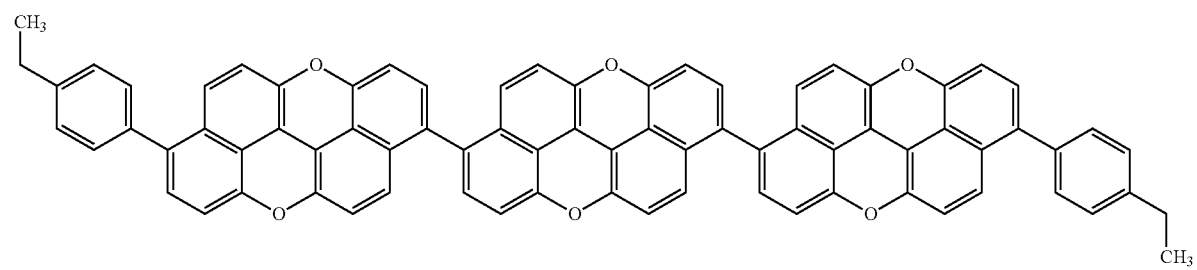

EXAMPLE 3

Example 3 is concerned with the anthanthrene based compound according to the second embodiment. The anthanthrene based compound of Example 3 is an anthanthrene based compound represented by the following structural formula (2) (oligo dichalcogeno anthanthrene based compound).

(2)

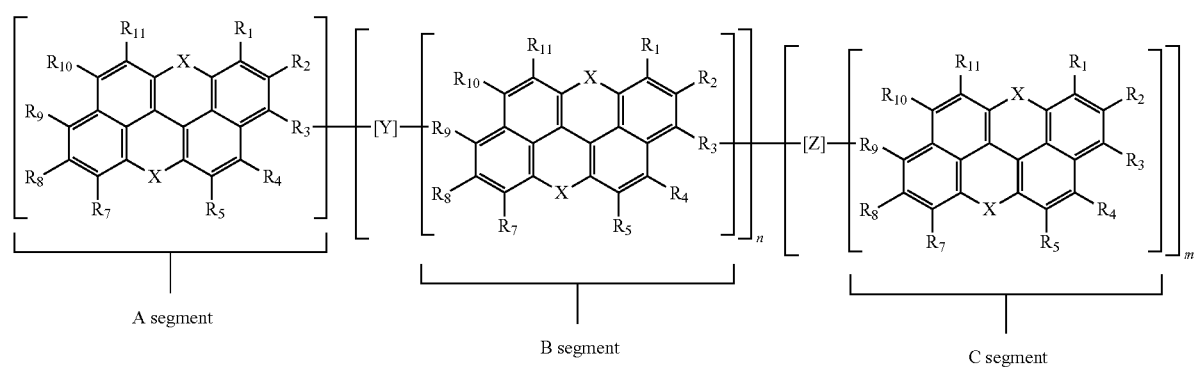

In the foregoing formula (2),

X represents an element belonging to the Group 16;

n represents an integer of from 0 to 20;

m represents an integer of from 1 to 9; and each of [Y] and [Z] independently represents a functional group of one member selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, an acyloxy group, an amide group, a carbamoyl group, a ureido group, an sulfinyl group, an alkylsulfonyl group, an arylsulfonyl group, an amino group, a fluorinated hydrocarbon group, a cyano group, a nitro group, a hydroxyl group, a mercapto group and a silyl group.

Also, a bonding position in the A segment to [Y] is at least one of from the 1-position to the 5-position and from the 7-position to the 11-position; a bonding position in the B segment to [Y] is at least one of from the 1-position to the 5-position and from the 7-position to the 11-position; a bonding position in the B segment to [Z] is at least one of from the 1-position to the 5-position and from the 7-position to the 11-position; and a bonding position in the C segment to [Z] is at least one of from the 1-position to the 5-position and from the 7-position to the 11-position.

In Example 3, X is an oxygen (O) element; n is 0; and m is 1. Therefore, the B segment and [Y] do not exist; and a different reading is given such that a bonding position in the A segment to [Z] is at least one of from the 1-position to the 5-position and from the 7-position to the 11-position. Specifically, the bonding position in the A segment to [Z] is one site at the 3-position; and the bonding position in the C segment to [Z] is one site at the 10-position. Also, in the A segment, each of the substituents $R_1$, $R_2$, $R_4$, $R_5$, $R_7$, $R_8$, $R_{10}$ and $R_{11}$ is a hydrogen atom; and $R_9$ is an arylalkyl group, specifically, an ethylaryl group, and more specifically an ethylphenyl group. Also, in the C segment, each of the substituents $R_1$, $R_2$, $R_4$, $R_5$, $R_7$, $R_8$, $R_{10}$ and $R_{11}$ is a hydrogen atom; and $R_3$ is an arylalkyl group, specifically, an ethylaryl group, and more specifically an ethylphenyl group. Furthermore, [Z] is an aryl group, and specifically a phenyl group.

Figure 2:
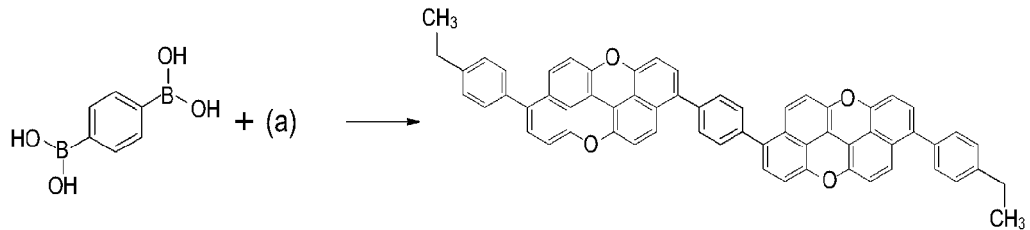
FIG. 2 is a drawing showing a synthesis scheme of an anthanthrene based compound of Example 3.

More specifically, the anthanthrene based compound of Example 3 is represented by the following structural formula (5). Also, a synthesis scheme of the anthanthrene based compound of Example 3 is shown in FIG. 2. That is, p-phenylenediboronic acid and 2 equivalents of the compound (a) are subjected to the Suzuki-Miyaura cross-coupling reaction in the presence of a palladium catalyst, whereby a compound represented by the structural formula (5) can be obtained.

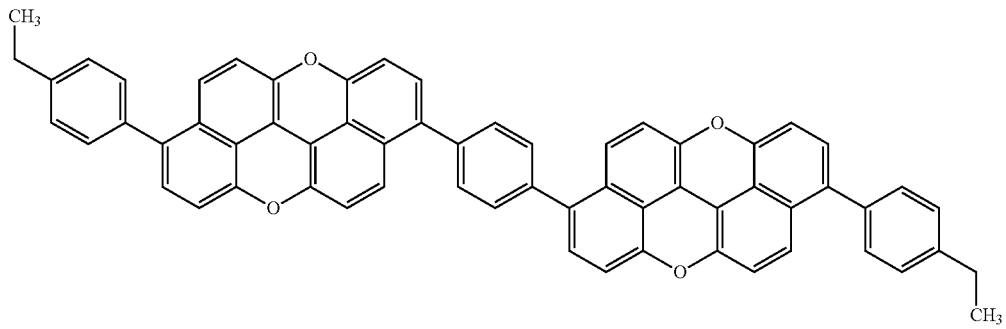

(5)

In Example 3, for example, n can also be set to be 1. Specifically, for example, the bonding position in the A segment to [Y] is set to be one site at the 3-position, and the bonding position in the B segment to [Y] is set to be one site at the 10-position. Also, the bonding position in the B segment to [Z] is set to be one site at the 3-position, and the bonding position in the C segment to [Z] is set to be one site at the 10-position. Also, in the A segment, each of the substituents $R_1$, $R_2$, $R_4$, $R_5$, $R_7$, $R_8$, $R_{10}$ and $R_{11}$ is a hydrogen atom; and $R_9$ is an arylalkyl group, specifically, an ethylaryl group, and more specifically an ethylphenyl group. Also, in the B segment, each of the substituents $R_1$, $R_2$, $R_4$, $R_5$, $R_7$, $R_8$, $R_{10}$ and $R_{11}$ is a hydrogen atom. Furthermore, in the C segment, each of the substituents $R_1$, $R_2$, $R_4$, $R_5$, $R_7$, $R_8$, $R_{10}$ and $R_{11}$ is a hydrogen atom; and $R_3$ is an arylalkyl group, specifically, an ethylaryl group, and more specifically an ethylphenyl group. Moreover, [Y] is an aryl group, and specifically a phenyl group. Also, [Z] is an alkyl group, and specifically an ethyl group.

EXAMPLE 4

Example 4 is concerned with each of the semiconductor devices according to the first embodiment and second embodiment. The semiconductor device of Example 5 (specifically, a field effect transistor (FET)) includes a substrate having thereon a gate electrode, a gate insulating layer, source/drain electrodes and a channel-forming region, wherein the channel-forming region is composed of the anthanthrene based compound represented by the foregoing structural formula (1). Alternatively, the semiconductor device of Example 4 includes a substrate having thereon a gate electrode, a gate insulating layer, source/drain electrodes and a channel-forming region, wherein the channel-forming region is composed of the anthanthrene based compound represented by the foregoing structural formula (2).

Figure 3A:
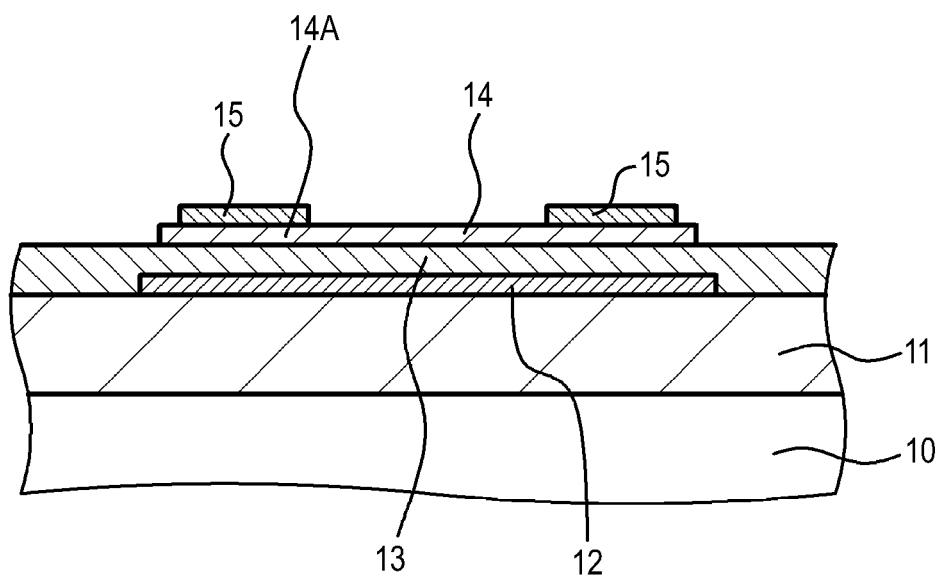
FIG. 3A is a schematic partial sectional view of a so-called bottom gate/top contact type field effect transistor.

More specifically, as shown in a schematic partial sectional view of FIG. 3A, the semiconductor device of Example 4 is a so-called bottom gate/top contact type FET (more specifically, TFT), including (A) a gate electrode 12 formed on substrates 10, 11;

(B) a gate insulating layer 13 formed on the gate electrode 12;

(C) a channel-forming region 14 and a channel-forming region extension 14A formed on the gate insulating layer 13; and (D) source/drain electrodes 15 formed on the channel-forming region extension 14A.

The substrates 10, 11 are constituted of a substrate 10 composed of a glass substrate and an insulating film 11 formed on the surface thereof and made of $SiO_2$; each of the gate electrode 12 and the source/drain electrodes 15 is composed of a metal thin film; and the gate insulating layer 13 is made of $SiO_2$. Also, each of the channel-forming region 14 and the channel-forming region extension 14A is constituted of any one of the anthanthrene based compounds described in Examples 1 to 3. Here, more specifically, each of the gate electrode 12 and the gate insulating layer 13 is formed on the insulating film 11.

An outline of a manufacturing method of the bottom gate/top contact type FET (specifically, TFT) is hereunder described.

[Step 500A]

First of all, the gate electrode 12 is formed on the substrate (the glass substrate 10 in which the insulating film 11 made of $SiO_2$ is formed on the surface thereof). Specifically, a resist layer (not shown) in which a portion where the gate electrode 12 is to be formed is removed is formed on the insulating film 11 on the basis of a lithography technology. Thereafter, a chromium (Cr) layer (not shown) as a contact layer and a gold (Au) layer as the gate electrode 12 are deposited in success over the whole surface by a vacuum vapor deposition method, and the resist layer is then removed. The gate electrode 12 can be thus obtained on the basis of a so-called lift-off method.

[Step 510A]

Subsequently, the gate insulating layer 13 is formed on the substrate (insulating film 11) including the gate electrode 12. Specifically, the gate insulating layer 13 made of $SiO_2$ is formed on the gate electrode 12 and the insulating film 11 on the basis of a sputtering method. During depositing the gate insulating layer 13, by covering a part of the gate electrode 12 by a hard mask, a discharge part (not shown) of the gate electrode 12 can be formed without adopting a photolithography process.

[Step 520A]

Subsequently, the channel-forming region 14 and the channel-forming region extension 14A are formed on the gate insulating layer 13. Specifically, any one of the anthanthrene based compounds described in the foregoing Examples 1 to 3 is deposited on the basis of a vacuum vapor deposition method.

[Step 530A]

Thereafter, the source/drain electrodes 15 are formed on the channel-forming region extension 14A so as to interpose the channel-forming region 14 therebetween. Specifically, a chromium (Cr) layer (not shown) as a contact layer and gold (Au) layers as the source/drain electrodes 15 are formed in success over the whole surface on the basis of a vacuum vapor deposition method. A structure shown in FIG. 3A can be thus obtained. During depositing the source/drain electrodes 15, by covering a part of the channel-forming region extension 14A by a hard mask, the source/drain electrodes 15 can be formed without adopting a photolithography process.

[Step 540A]

Finally, an insulating layer (not shown) which is a passivation film is formed over the whole surface; an opening is formed on the insulating layer in an upper part of the source/drain electrodes 15; a wiring material layer is formed over the whole surface including the inside of the opening; and the wiring material layer is then subjected to patterning. Thus, a bottom gate/top contact type FET (TFT) in which wirings (not shown) connected to the source/drain electrodes 15 are formed on the insulating layer can be obtained.

FET is not limited to the so-called bottom gate/top contact type shown in FIG. 3A, but besides, FET can also be formed in a so-called bottom gate/bottom contact type, a so-called top gate/top contact type or a so-called top gate/bottom contact type.

Figure 3B:
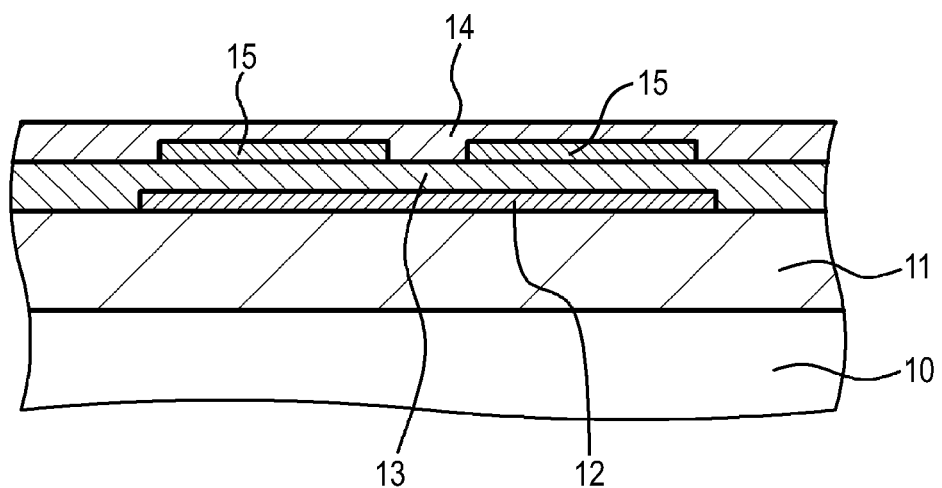
FIG. 3B is a schematic partial sectional view of a so-called bottom gate/bottom contact type field effect transistor.

A so-called bottom gate/bottom contact type FET (more specifically, TFT), a schematic partial sectional view of which is shown in FIG. 3B, includes (A) a gate electrode 12 formed on substrates 10, 11;

(B) a gate insulating layer 13 formed on the gate electrode 12;

(C) source/drain electrodes 15 formed on the gate insulating layer 13; and (D) a channel-forming region 14 located between the source/drain electrodes 15 and formed on the gate insulating layer 13.

An outline of a manufacturing method of the bottom gate/bottom contact type TFT is hereunder described.

[Step 500B]

First of all, similar to the Step 500A, the gate electrode 12 is formed on the substrate (insulating film 11); and thereafter, similar to the Step 510A, the gate insulating layer 13 is formed on the gate electrode 12 and the insulating film 11.

[Step 510B]

Subsequently, the source/drain electrodes 15 composed of a gold (Au) layer are formed on the gate insulating layer 13. Specifically, a resist layer in which a portion where the source/drain electrodes 15 are to be formed is removed is formed on the basis of a lithography technology. Then, similar to the Step 500A, a chromium (Cr) layer (not shown) as a contact layer and a gold (Au) layer as the source/drain electrodes 15 are deposited on the resist layer and the gate insulating layer 13 in success by a vacuum vapor deposition method, and thereafter, the resist layer is removed. The source/drain electrodes 15 can be thus obtained on the basis of a so-called lift-off method.

[Step 520B]

Thereafter, the channel-forming region 14 is formed on a portion of the gate insulating layer 13 located between the source/drain electrodes 15 on the basis of the same manner as in the Step 520A. A structure shown in FIG. 3B can be thus obtained.

[Step 530B]

Finally, by executing the same step as in the Step 540A, the bottom gate/bottom contact type FET (TFT) can be obtained.

Figure 4A:
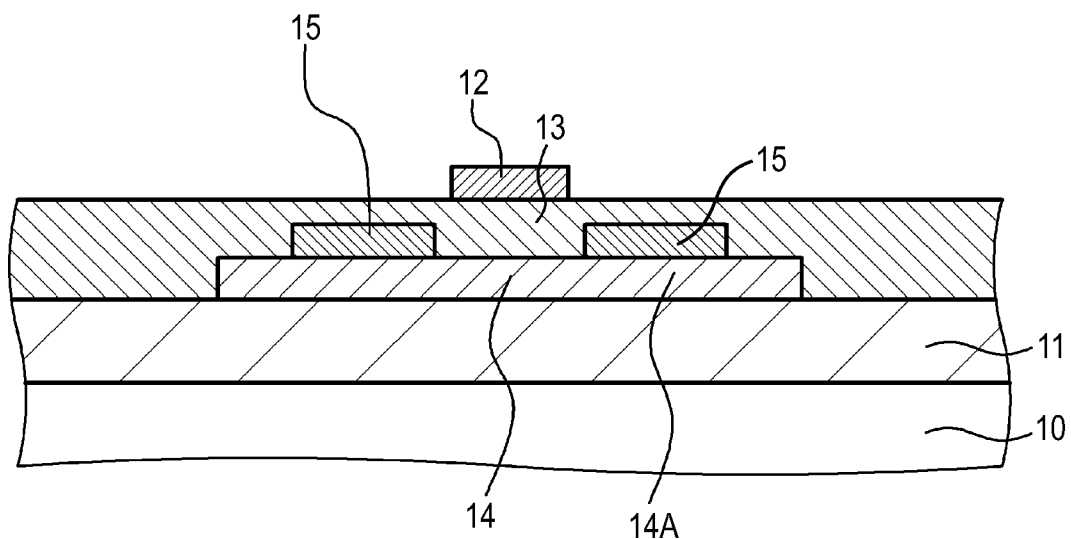
FIG. 4A is a schematic partial sectional view of a so-called top gate/top contact type field effect transistor.

A so-called top gate/top contact type FET (more specifically, TFT), a schematic partial sectional view of which is shown in FIG. 4A, includes (A) a channel-forming region 14 and a channel-forming region extension 14A formed on substrates 10, 11;

(B) source/drain electrodes 15 formed on the channel-forming region extension 14A;

(C) a gate insulating layer 13 formed on the source/drain electrodes 15 and the channel-forming region 14; and (D) a gate electrode 12 formed on the gate insulating layer 13.

An outline of a manufacturing method of the top gate/top contact type TFT is hereunder described.

[Step 500C]

First of all, the channel-forming region 14 and the channel-forming region extension 14A are formed on the substrate (the glass substrate 10 in which the insulating film 11 made of $SiO_2$ is formed on the surface thereof) on the basis of the same method as in the Step 520A.

[Step 510C]

Subsequently, the source/drain electrodes 15 are formed on the channel-forming region extension 14A so as to interpose the channel-forming region 14 therebetween. Specifically, a chromium (Cr) layer (not shown) as a contact layer and gold (Au) layers as the source/drain electrodes 15 are formed in success over the whole surface on the basis of a vacuum vapor deposition method. During depositing the source/drain electrodes 15, by covering a part of the channel-forming region extension 14A by a hard mask, the source/drain electrodes 15 can be formed without adopting a photolithography process.

[Step 520C]

Subsequently, the gate insulating layer 13 is formed on the source/drain electrodes 15 and the channel-forming region 14. Specifically, by depositing PVA over the whole surface by a spin coating method, the gate insulating layer 13 can be obtained.

[Step 530C]

Thereafter, the gate electrode 12 is formed on the gate insulating layer 13. Specifically, a chromium (Cr) layer (not shown) as a contact layer and a gold (Au) layer as the gate electrode 12 are deposited in success over the whole surface on the basis of a vacuum vapor deposition method. A structure shown in FIG. 4A can be thus obtained. During depositing the gate electrode 12, by covering a part of the gate insulating layer 13 by a hard mask, the gate electrode 12 can be formed without adopting a photolithography process. Finally, by executing the same step as in the Step 540A, the top gate/top contact type FET (TFT) can be obtained.

Figure 4B:
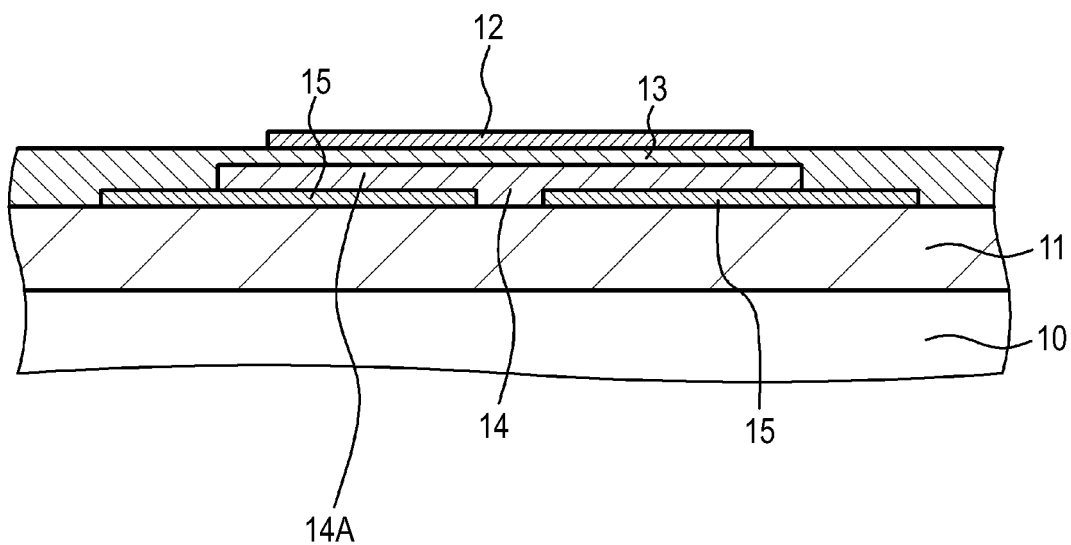
FIG. 4B is a schematic partial sectional view of a so-called top gate/bottom contact type field effect transistor.

A so-called top gate/bottom contact type FET (more specifically, TFT), a schematic partial sectional view of which is shown in FIG. 4B, includes (A) source/drain electrodes 15 formed on substrates 10, 11;

(B) a channel-forming region 14 formed on the substrates 10, 11 located between the source/drain electrodes 15;

(C) a gate insulating layer 13 formed on the channel-forming region 14; and (D) a gate electrode 12 formed on the gate insulating layer 13.

An outline of a manufacturing method of the top gate/bottom contact type TFT is hereunder described.

[Step 500D]

First of all, the source/drain electrodes 15 are formed on the substrate (the glass substrate 10 in which the insulating film 11 made of $SiO_2$ is formed on the surface thereof). Specifically, a chromium (Cr) layer (not shown) as a contact layer and gold (Au) layers as the source/drain electrodes 15 are formed on the basis of a vacuum vapor deposition method. During depositing the source/drain electrodes 15, by covering a part of the substrate (insulating film 11) by a hard mask, the source/drain electrodes 15 can be formed without adopting a photolithography process.

[Step 510D]

Thereafter, the channel-forming region 14 is formed on the substrate (insulating film 11) located between the source/drain electrodes 15 on the basis of the same manner as in the Step 520A. Actually, a channel-forming region extension 14A is formed on the source/drain electrodes 15.

[Step 520D]

Subsequently, the gate insulating layer 13 is formed on the source/drain electrodes 15 and the channel-forming region 14 (actually, on the channel-forming region 14 and the channel-forming region extension 14A) in the same manner as in the Step 520C.

[Step 530D]

Thereafter, the gate electrode 12 is formed on the gate insulating layer 13 in the same manner as in the Step 530C. A structure shown in FIG. 4B can be thus obtained. Finally, by executing the same step as in the Step 540A, the top gate/bottom contact type FET (TFT) can be obtained.

The present application has been described on the basis of the preferred Examples. However, it should not be construed that the present application is limited to these Examples. The structures and configurations, the manufacturing conditions and the manufacturing methods of the semiconductor devices are merely exemplification and can be properly changed. In the case where the semiconductor devices obtained by the embodiments according to the present application are applied to or used for display devices or various electronic appliances, monolithic integrated circuits in which a number of FETs are integrated on a support or a supporting member may be fabricated, or the individual FETs may be used upon being separated by cutting to produce discrete components.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:
1. A semiconductor device comprising:
a substrate having thereon
a gate electrode,
a gate insulating layer,
source/drain electrodes, and
a channel-forming region, wherein
the channel-forming region is composed of a anthanthrene based compound represented by the following structural formula (2):

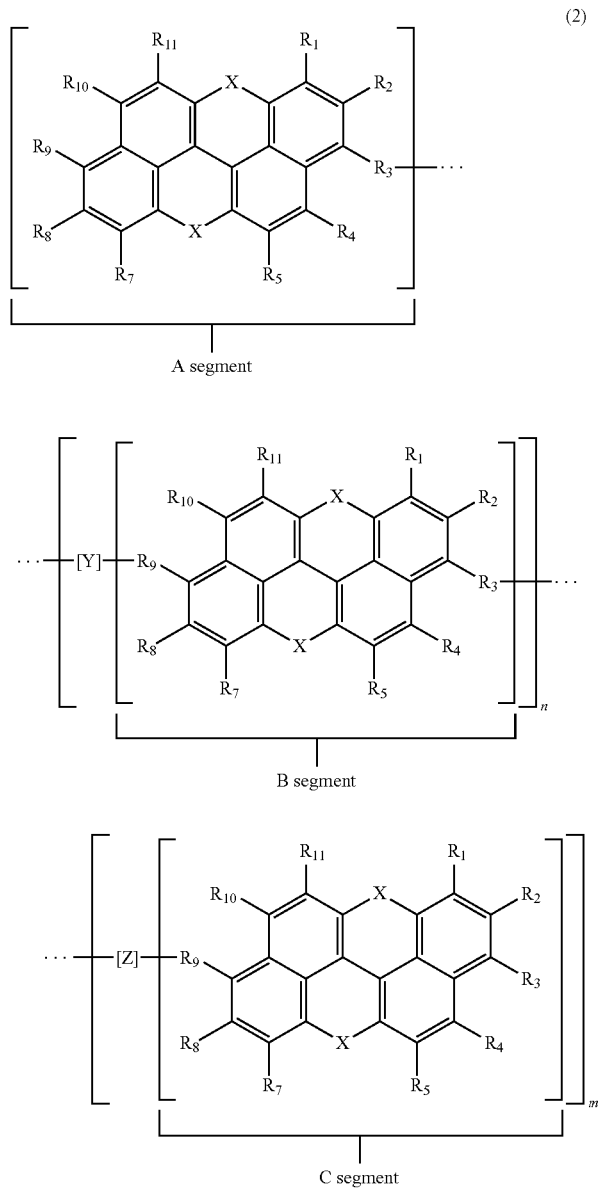

wherein
X represents oxygen;
n represents an integer of from 1 to 20;
m represents an integer of from 1 to 9;
a bonding position in the A segment to the B segment is at least one of from the 1-position to the 5-position and from the 7-position to the 11-position;
a bonding position in the B segment to the A segment is at least one of from the 1-position to the 5-position and from the 7-position to the 11-position;
a bonding position in the B segment to the C segment is at least one of from the 1-position to the 5-position and from the 7-position to the 11-position;
a bonding position in the C segment to the B segment is at least one of from the 1-position to the 5-position and from the 7-position to the 11-position; and
each of [Y] represents a phenyl group and [Z] represents an ethyl group,
wherein each of the substituents $R_1$, $R_2$, $R_3$, $R_4$, $R_5$, $R_7$, $R_8$, $R_9$, $R_{10}$ and $R_{11}$ independently represents a substituent selected from the group consisting of hydrogen, an alkyl group, an alkenyl group, an aryl group, an arylalkyl group, an aromatic heterocyclic ring and a halogen atom.

* * * * *